(12) United States Patent
Burbar et al.

(10) Patent No.: US 12,048,572 B2
(45) Date of Patent: *Jul. 30, 2024

(54) LIGHTING ARRANGEMENT FOR A MEDICAL IMAGING SYSTEM

(71) Applicant: Siemens Medical Solutions USA, Inc., Malvern, PA (US)

(72) Inventors: Ziad Burbar, Knoxville, TN (US); James L. Corbeil, Knoxville, TN (US); Jeffrey Bostrom, Clinton, TN (US); James Williams, Knoxville, TN (US); Michael Dulude, North Barrington, IL (US); Keith Gerlach, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/349,249

(22) Filed: Jul. 10, 2023

(65) Prior Publication Data

US 2023/0346325 A1     Nov. 2, 2023

Related U.S. Application Data

(63) Continuation of application No. 18/188,513, filed on Mar. 23, 2023, now Pat. No. 11,793,474, which is a
(Continued)

(51) Int. Cl.
*A61B 6/08* (2006.01)
*A61B 6/03* (2006.01)
*A61B 90/00* (2016.01)

(52) U.S. Cl.
CPC .............. *A61B 6/08* (2013.01); *A61B 6/032* (2013.01); *A61B 6/037* (2013.01); *A61B 90/36* (2016.02);
(Continued)

(58) Field of Classification Search
CPC .......... A61B 90/36; A61B 6/032; A61B 6/08; A61B 6/037; A61B 2090/3618;
(Continued)

(56) References Cited

U.S. PATENT DOCUMENTS 4,234,907 A    11/1980  Daniel
5,307,245 A     4/1994  Myers et al.
(Continued)

FOREIGN PATENT DOCUMENTS

EP       0495273 B1    9/1996
WO    2019165302 A1    8/2019

OTHER PUBLICATIONS

Closed MRI Bore Light, 2023, printout from webpage <https://www.lumitex.com/success-stories/map/closed-mri-bore-light?_hstc=117255833.acd12a5550eda9df8b4539b106cb309e.1582749504043.1586%E2%80%A6>, pp. 1-5, Lumitex, LLC, Strongsville, Ohio.
(Continued)

*Primary Examiner* — Irakli Kiknadze

(57) ABSTRACT

A lighting arrangement for a medical imaging system having a cylindrical wall that forms a tunnel that receives a patient to be scanned. The lighting arrangement includes a light transmitting section aligned on a longitudinal axis of the imaging system wherein the light transmitting section forms a part of the tunnel. The lighting arrangement also includes a reflector section that is radially outside the light transmitting section. In addition, the lighting arrangement includes at least one lighting device located between the reflector section and light transmitting section wherein the lighting device emits light that is reflected by the reflector section onto the light transmitting section and wherein the light is then transmitted through the light transmitting section and into the tunnel to circumferentially illuminate the tunnel.

22 Claims, 8 Drawing Sheets

Related U.S. Application Data continuation of application No. 16/949,229, filed on Oct. 21, 2020, now Pat. No. 11,647,971.

(52) U.S. Cl.
CPC ............... *A61B 2090/3614* (2016.02); *A61B 2090/3618* (2016.02)

(58) Field of Classification Search
CPC ...... A61B 2090/3614; A61B 2090/309; A61B 6/035; A61B 6/04; A61B 6/4417; A61B 6/461; A61B 6/0492; A61B 6/105; A61B 6/12; A61B 6/4225; A61B 6/4441; A61B 6/547; A61B 90/08; A61B 90/13; A61B 90/25; A61B 90/37; A61B 90/39; A61B 90/50; A61B 2017/0092; A61B 2090/3764; A61B 2090/3937; A61B 2090/3983; A61B 90/11; A61B 5/0555; A61B 5/486; A61B 6/0407; A61B 6/467; A61B 5/055; A61B 6/102; A61B 6/5294; A61B 6/464; G01R 33/283; G01R 33/481; G01R 33/28; A61M 21/02; A61M 21/00
USPC ........................................................ 378/206
See application file for complete search history.

(56) References Cited

U.S. PATENT DOCUMENTS

| | | | |
|---|---|---|---|
| 5,469,488 | A | 11/1995 | Ono |
| 5,568,964 | A | 10/1996 | Parker et al. |
| 5,613,751 | A | 3/1997 | Parker et al. |
| 9,316,387 | B1 * | 4/2016 | Olsson ............... F21V 5/04 |
| 11,647,971 | B2 * | 5/2023 | Burbar ............... A61B 6/08 378/206 |
| 11,793,474 | B2 * | 10/2023 | Burbar ............... A61B 90/36 |
| 2002/0065461 | A1 | 5/2002 | Cosman |
| 2003/0036692 | A1 | 2/2003 | Landi et al. |
| 2005/0004444 | A1 | 1/2005 | Boninger et al. |
| 2009/0154647 | A1 | 6/2009 | Matsukawa |
| 2010/0056902 | A1 | 3/2010 | Granzer et al. |
| 2013/0345543 | A1 | 12/2013 | Steibel, Jr. et al. |
| 2019/0143145 | A1 | 5/2019 | Laurence, Jr. |
| 2021/0345976 | A1 | 11/2021 | Brown et al. |
| 2022/0117565 | A1 | 4/2022 | Burbar et al. |

OTHER PUBLICATIONS

Dan Whitaker, Imaging: A Tale of Two Cities, printout from webpage <https://www.siemens-healthineers.com/en-us/computed-tomography/news/mso-imaging-a-tale-of-two-cities.html>, Nov. 2018, pp. 5-6, SOMATOM Sessions, Siemens Medical Solutions USA, Inc., Malvern, Pennsylvania.

* cited by examiner

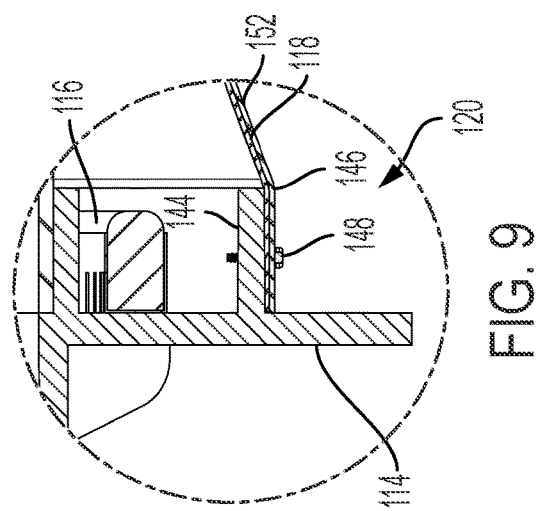
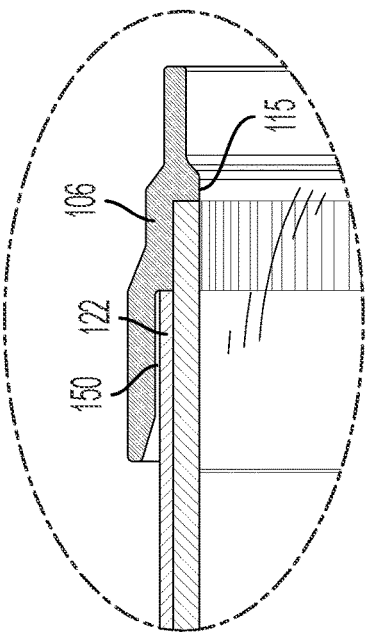
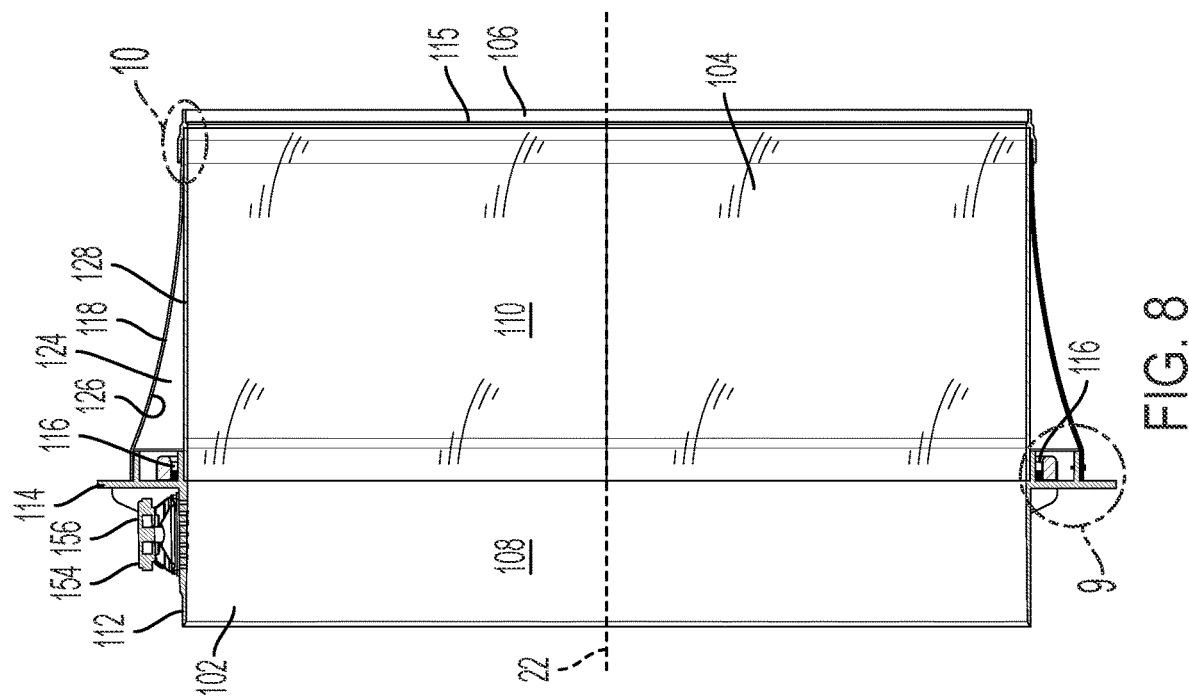

LIGHTING ARRANGEMENT FOR A MEDICAL IMAGING SYSTEM

CROSS REFERENCE TO RELATED APPLICATIONS

This application is a continuation-in-part of copending U.S. application Ser. No. 18/188,513, filed Mar. 23, 2023 and issued on Oct. 24, 2023 as U.S. Pat. No. 11,793,474, which is a continuation of U.S. application Ser. No. 16/949,229, filed Oct. 21, 2020 and issued on May 16, 2023 as U.S. Pat. No. 11,647,971 entitled LIGHTING ARRANGEMENT FOR A MEDICAL IMAGING SYSTEM each of which are hereby incorporated by reference herein in their entirety.

TECHNICAL FIELD

Aspects of the present invention relate to a lighting arrangement for illuminating a patient tunnel of a medical imaging system, and more particularly, to a lighting arrangement for a medical imaging system having a cylindrical wall that forms a tunnel that receives a patient to be scanned. The lighting arrangement includes a light transmitting section aligned on a longitudinal axis of the imaging system wherein the light transmitting section forms a part of the tunnel. The lighting arrangement also includes a reflector section that is radially outside the light transmitting section. In addition, the lighting arrangement includes at least one lighting device located between the reflector section and light transmitting section wherein the lighting device emits light that is reflected by the reflector section onto the light transmitting section and wherein the light is then transmitted through the light transmitting section and into the tunnel to circumferentially illuminate the tunnel.

BACKGROUND

Medical imaging systems include a patient bore that receives a patient to be imaged or scanned. The bore is typically elongated and forms a cylindrically shaped patient tunnel through which the patient is moved in a longitudinal direction along a longitudinal axis of the tunnel. The tunnel may be imposing or intimidating to those that are either young or for adults who suffer from claustrophobia, for example. This effect is becoming more pronounced as the average bore length of medical imaging systems, such as positron-emission tomography/computed tomography (PET/CT) systems, is trending longer. In particular, imaging systems having extended axial field-of-views (FoVs), coupled with bore diameters that have remained largely unchanged, have made PET systems less appealing since patients frequently experience a "closed-space feeling" or claustrophobia when located in the tunnel. This is especially true in imaging systems having even longer tunnels such as MR-PET imaging systems and imaging systems having FoVs that are a meter long or more.

The addition of light in the tunnel ameliorates the look and feel of the system and gives the tunnel an appearance of being spacious, thus lessening the effects of claustrophobia. For example, lights may be incorporated into the front and back covers of the tunnel. In addition, light projectors located on the longitudinal axis of the tunnel may be used to direct light in a longitudinal direction through the tunnel.

SUMMARY OF THE INVENTION

A lighting arrangement is disclosed for a medical imaging system having a cylindrical wall that forms a tunnel that receives a patient to be scanned. The lighting arrangement includes a light transmitting section aligned on a longitudinal axis of the imaging system wherein the light transmitting section forms a part of the tunnel. The lighting arrangement also includes a reflector section that is radially outside the light transmitting section. In addition, the lighting arrangement includes at least one lighting device located between the reflector section and light transmitting section wherein the lighting device emits light that is reflected by the reflector section onto the light transmitting section and wherein the light is then transmitted through the light transmitting section and into the tunnel to circumferentially illuminate the tunnel.

In addition, a method is disclosed of illuminating a tunnel of a medical imaging system having a cylindrical wall that forms a tunnel that receives a patient to be scanned wherein the medical imaging system includes first and second imaging portions having first and second fields of view. The method includes providing a light transmitting section aligned on a longitudinal axis of the imaging system wherein the light transmitting section forms a part of the tunnel. The method also includes providing a reflector section that is radially outside the light transmitting section. In addition, the method includes providing light that is reflected by the reflector section onto the light transmitting section wherein the light is then transmitted through the light transmitting section and into the tunnel to circumferentially illuminate the tunnel.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which:

FIG. 8 is a cross-sectional side view of the further alternate embodiment of the lighting arrangement.

FIG. 9 is an enlarged view of balloon section 9 of FIG. 8 and depicts portions of a reflector section and flange portion.

FIG. 10 is an enlarged view of balloon section 10 of FIG. 8 and depicts portions of a mounting trim section.

DETAILED DESCRIPTION

Figure 1:
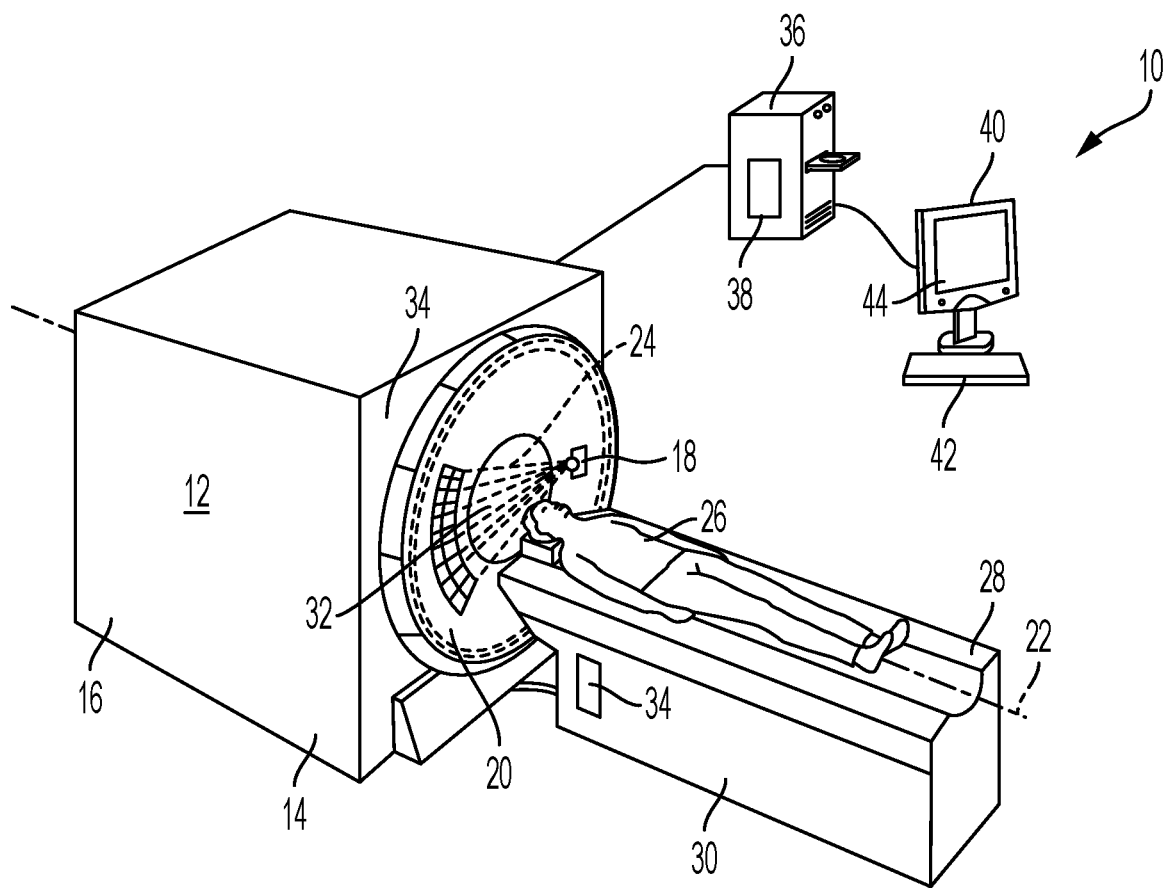
FIG. 1 depicts a medical imaging system in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a view of an exemplary medical imaging system 10 in accordance with an aspect of the invention is shown. The invention may be used in conjunction with any medical imaging system 10 having a patient tunnel for receiving a patient such as a magnetic resonance imaging (MRI) system, a positron emission tomography (PET) system, a single-photon emission computed tomography (SPECT) system, a PET/MRI system, an X-ray computed tomography (CT) system, a PET/CT system, a SPECT/CT system and others. For purposes of illustration, the invention will be described in connection with a PET/CT imaging system 12 having a CT portion 14 and a PET portion 16. The CT portion 14 includes a recording unit, comprising an X-ray source 18 and an X-ray detector 20. The recording unit rotates about a longitudinal axis 22 during the recording of a tomographic image, and the X-ray source 18 emits X-rays 24 during a recording. While an image is being recorded a patient 26 lies on a patient bed 28. The bed 28 is connected to a table base 30 such that it supports the bed 28 bearing the patient 26. The bed 28 is designed to move the patient 26 along a recording direction through an opening or tunnel 32 of a gantry 34 of the system 12. The table base 30 includes a control unit 34 connected to a computer 36 to exchange data. In the example shown in FIG. 1, a medical diagnostic or therapeutic unit is designed in the form of a system 12 by a determination unit 38 in the form of a stored computer program that can be executed on the computer 36. The computer 36 is connected to an output unit 40 and an input unit 42. The output unit 40 is, for example, one (or more) liquid crystal display (LCD) or plasma screen(s). An output 44 on the output unit 40 comprises, for example, a graphical user interface for actuating the individual units of the system 12 and the control unit 34. Furthermore, different views of the recorded data can be displayed on the output unit 40. The input unit 42 is for example a keyboard, mouse, touch screen or a microphone for speech input.

Figure 2A:
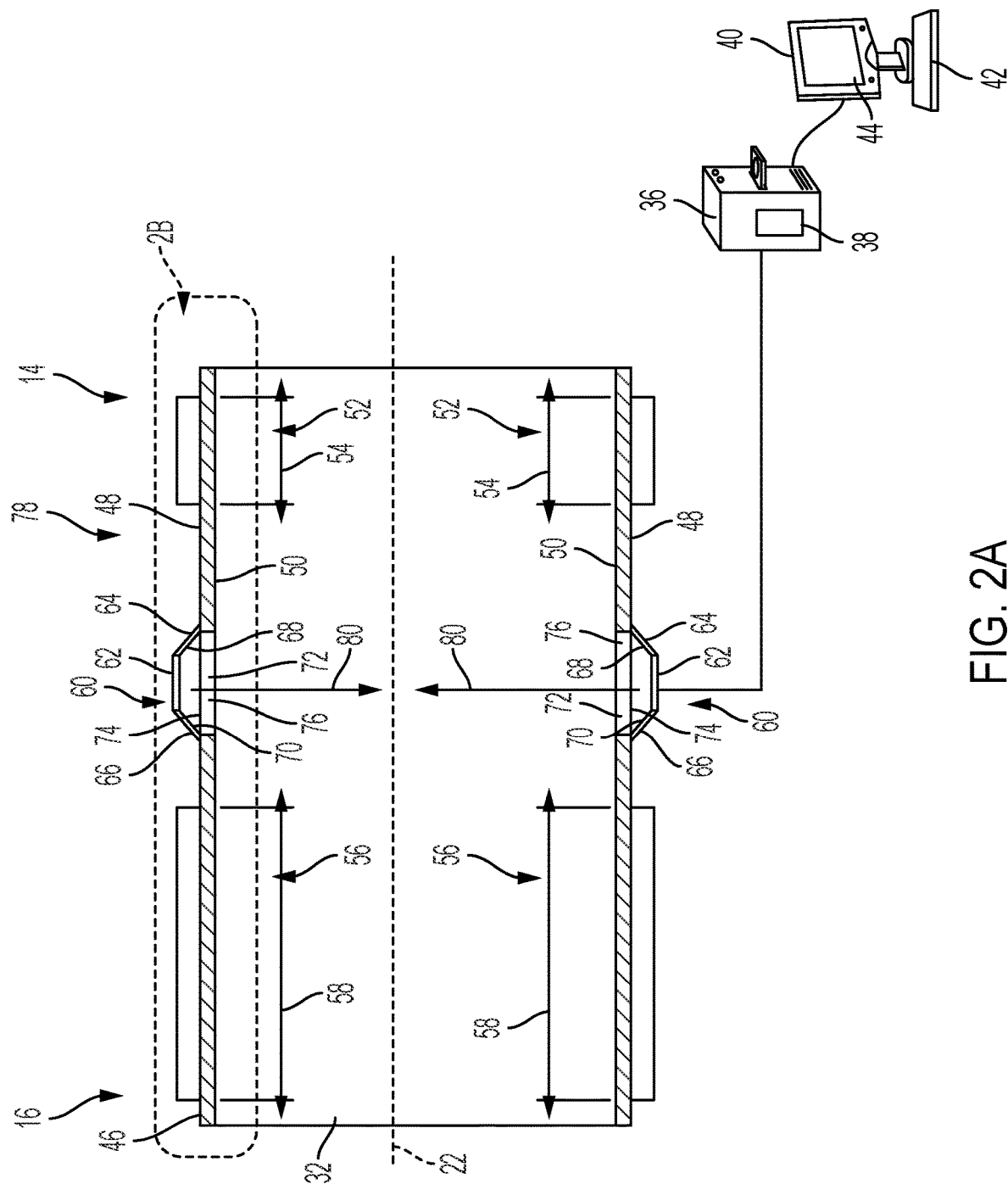
FIG. 2A depicts a lighting arrangement in accordance with an aspect of the invention.
Figure 3:
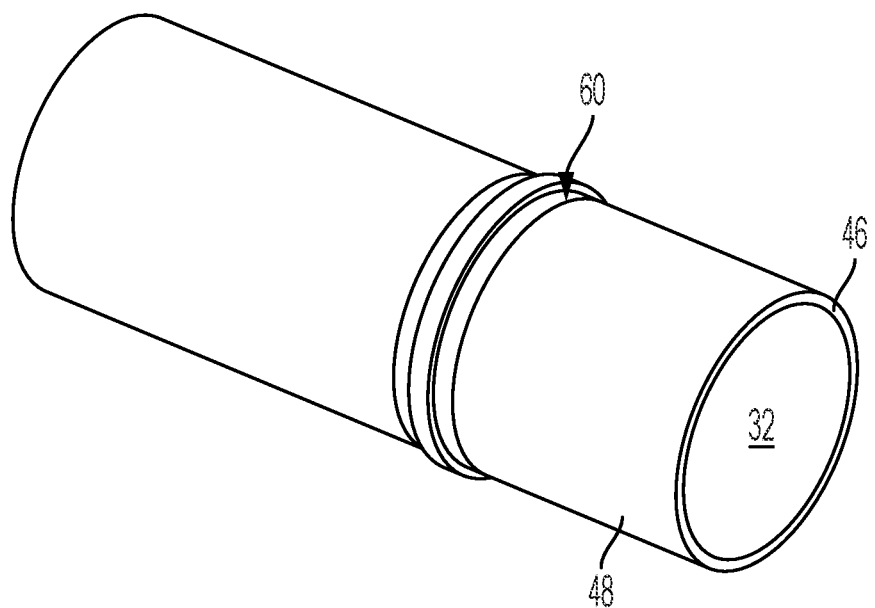
FIG. 3 is a perspective view of a wall and a lighting device.

FIG. 2A depicts a schematic cross-sectional side view of the tunnel 32. The tunnel 32 is defined by a substantially cylindrical tunnel wall 46 having outer 48 and inner 50 surfaces. The CT portion 14 includes a CT field of view 52 having a first width 54 and the PET portion 16 includes a PET field of view 56 having a second width 58. The CT 14 and PET 16 portions are sensitive to X-rays and gamma rays, respectively, via the CT 52 and PET 56 fields of view, respectively. In accordance with an aspect of the invention, a lighting device 60 is located adjacent to or on the outer surface 48 of the wall 46 and between the CT 52 and PET 56 fields of view. The lighting device 60 is also located outside of the first 54 and second 58 widths of the CT 52 and PET 56 fields of view, respectively, so that X-rays and gamma rays generated by the system 12 are not affected by the lighting device 60. FIG. 3 is a perspective view of the wall 46 and the lighting device 60. Referring to FIG. 3 in conjunction with FIG. 2A, the lighting device 60 may extend around an entire circumference of the outer surface 48 of the wall 46 to form a substantially ring-shaped configuration around the wall 46 having a central angle of 360 degrees. Alternatively, the lighting device 60 may extend only partially around the circumference of the outer surface 48 to form a semicircular (i.e. approximately 180 degrees) shape or an arc shape of either more or less than 180 approximately degrees.

Figure 2B:
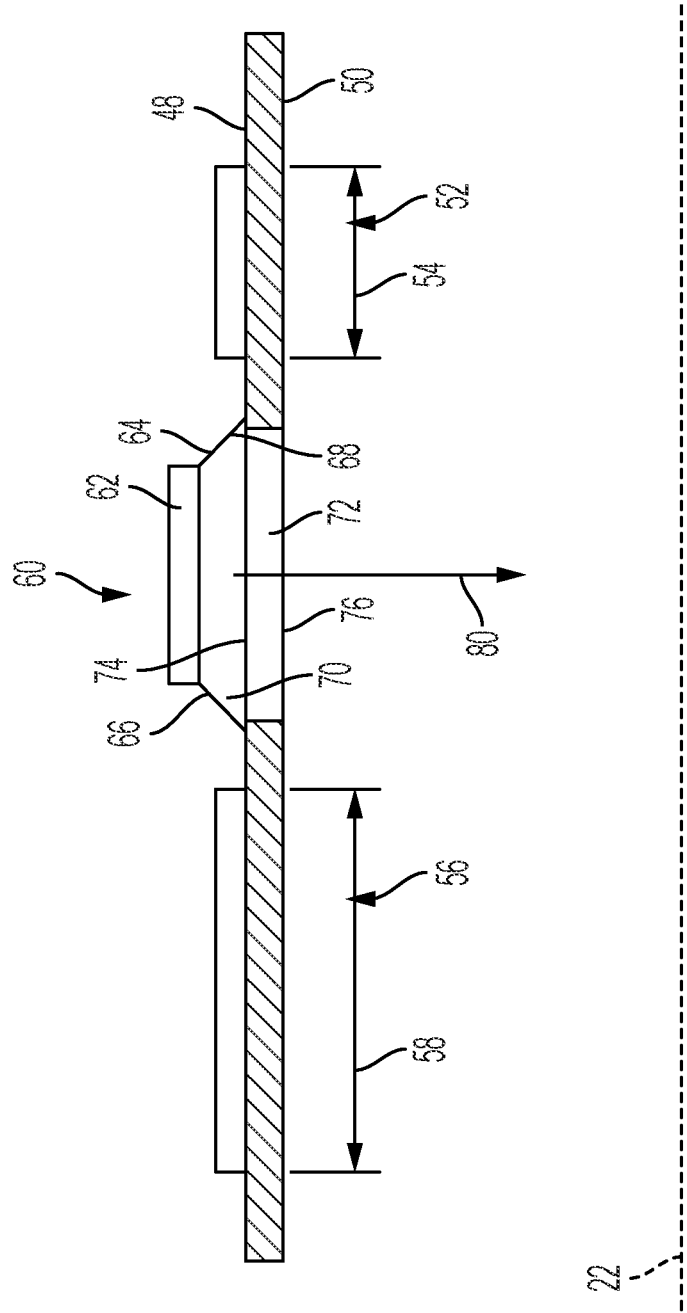
FIG. 2B is an enlarged view of region 2B of FIG. 2A.

FIG. 2B is an enlarged view of region 2B of FIG. 2A. Referring FIGS. 2A and 2B, the lighting device 60 includes a light source 62 located between first 64 and second 66 reflector elements that extend toward the outer surface 48 and contact the outer surface 48. The first 64 and second 66 reflector elements include first 68 and second 70 mirror surfaces, respectively, located to reflect light emitted by the light source 62. In an alternate embodiment, additional or fewer reflector elements and/or mirror surfaces may be used. The wall 46 includes a window or transparent wall section 72 having transparent outer 74 and inner 76 surfaces. In accordance with an aspect of the invention, the transparent inner surface 76 is aligned with the inner surface 50 of the wall 46 to form a continuously smooth inner surface. This reduces the likelihood that the patient 26 is caught or snagged when the patient 26 is moved in and out of the tunnel 32 and facilitates equipment hygiene. The transparent wall section 72 is aligned with the lighting device 60 to form a lighting arrangement 78 for illuminating the tunnel 32. In an embodiment, a light diffuser may be used instead of, or in addition to, the transparent wall section 72.

Light 80 emitted by the light source 62 travels toward the transparent wall section 72 and is reflected by the first 68 and second 70 mirror surfaces toward the transparent wall section 72. Light 80 is then transmitted through the transparent wall section 72 in a direction substantially orthogonal to the longitudinal axis 22 and into the tunnel 32 to illuminate the tunnel 32. Alternatively, light 80 may be oriented at an angle other than an orthogonal angle relative to the longitudinal axis 22. The light source 62 may be a strip of lights, a fiber optic light rope or a strip of red, green, blue (RGB) light emitting diodes (LEDs) or other light source that emits a broad light spectrum.

In an embodiment, the transparent wall section 72 corresponds to the circumferential shape of the lighting device 60. For example, the transparent wall section 72 and the lighting device 60 may both be ring-shaped such that light is transmitted through the entire circumference (i.e. 360 degrees) and into the tunnel 32 to circumferentially illuminate the tunnel 32. In an embodiment, the first 64 and second 66 reflector elements are sloped away from each other in order to provide a relatively wide-angle light beam in the tunnel 32. Alternatively, the first 64 and second 66 reflector elements may be oriented to provide other beam angles as desired, such as a relatively narrow beam angle.

Illumination of the tunnel 32 ameliorates the look and feel of the tunnel 32 and gives the tunnel 32 an appearance of being spacious to the patient 26, thus lessening the effects of claustrophobia and calming the patient 26. Further, the lighting arrangement 78 is located outside of both the CT 52 and PET 56 fields of view (i.e. outside of an imaging volume) and thus does not influence the X-rays or gamma rays generated by the system 12 and avoids attenuation and scatter of the signals.

In addition to illuminating the tunnel 32, the lighting arrangement 78 may be used to generate light that serves as a parameter indicator for a clinician or operator so that the operator is able to readily observe a status of the system 12 without having to be located at terminal or output unit 40 of the system 12. In accordance with an aspect of the invention, lighting in the tunnel 32 may be varied in intensity according to an amount of activity measured by the PET portion 16 such as a changing count rate. In addition, the lighting device 60 may provide color lighting indicative of a system status or mode to indicate that the system is on, idling, running, that the bed 28 or a patient handling system is in motion and others.

Different color lighting may be used to indicate the health of the system. For example, upon startup of the system 12, green lighting may be used to indicate a normal system operating status (i.e. ready to scan, no system issue detected and others), yellow lighting to indicate a system warning that needs attention, red lighting to indicate a system failure that needs to be resolved and blue lighting to indicate that the system 12 is in a power save mode. Further, different color lighting may be used to indicate a message or instruction to the patient. For example, a first color may be used to indicate to the patient to hold their breath, a second color to indicate to the patient that they should breathe and other colors may be used to indicate other messages. In addition, the light source 62 may be arranged in a panel configuration to form separate LEDs that each serve as pixels on a text screen. This enables the display of messages on the screen that are helpful to a patient 26 that has hearing loss or useful for studying a patient's auditory system response. For example, the messages indicating a patient instruction such as "breathe", "stop breathing", or a message indicating scan time, remaining scan time and others may be displayed on the screen. The computer 36 may be used to control activation and operation of the light source 62.

Figure 4:
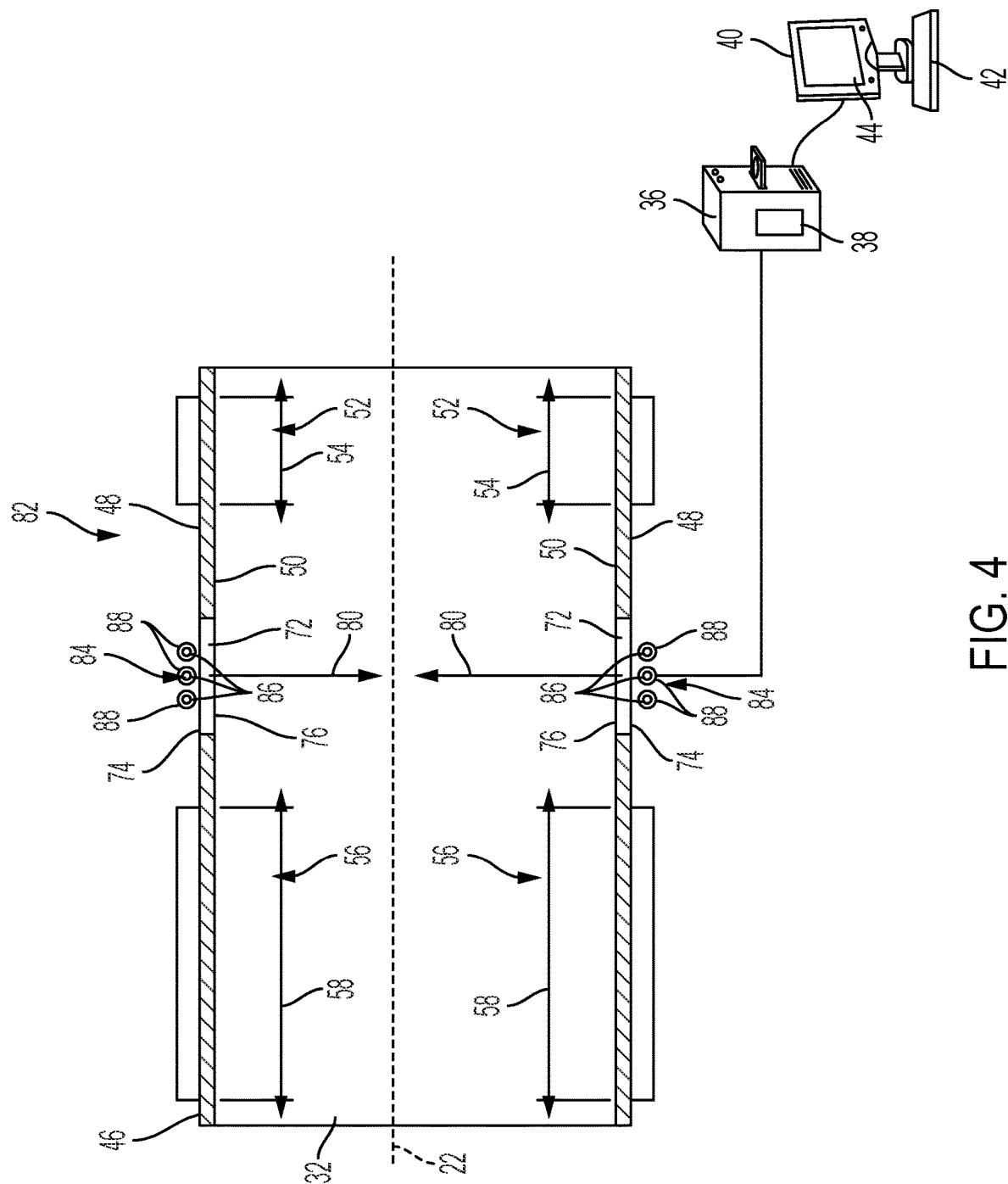
FIG. 4 depicts a lighting arrangement in accordance with an alternate embodiment of the invention.

Referring to FIG. 4, a lighting arrangement 82 for illuminating the tunnel 32 in accordance with an alternate embodiment of the invention is shown. Lighting device 84 includes at least one lighting element 86 inserted into a rope or light strip 88 of substantially transparent fiber optic material. In an embodiment, the lighting element 86 includes at least one RGB LED or other light source that emits different color light. The strip 88 is located on the transparent outer surface 74 and may extend around the entire circumference of the transparent outer surface 74 of the transparent wall section 72 to form a ring-shaped configuration having a central angle of 360 degrees around the wall 46. Alternatively, the strip 88 may extend only partially around the circumference of the transparent outer surface 74 to form a semicircular (i.e. approximately 180 degrees) shape or an arc shape of either more or less than 180 approximately degrees. More than one strip 88 may be positioned around the circumference of the transparent outer surface 74 such that the strips 88 are positioned side by side on the transparent outer surface 74 to a desired width. The strips 88 are located outside of the first 54 and second 58 widths of the CT 52 and PET 56 fields of view, respectively, so that X-rays and gamma rays generated by the system 12 are not affected by the strips 88. In an embodiment, light 80 emitted by the lighting device 84 is transmitted through the transparent wall section 72 in a direction substantially orthogonal to the longitudinal axis 22 such that light is transmitted through the entire circumference (i.e. 360 degrees) and into the tunnel 32 to circumferentially illuminate the tunnel 32. Alternatively, light 80 may be oriented at an angle other than an orthogonal angle relative to the longitudinal axis 22.

Figure 6:
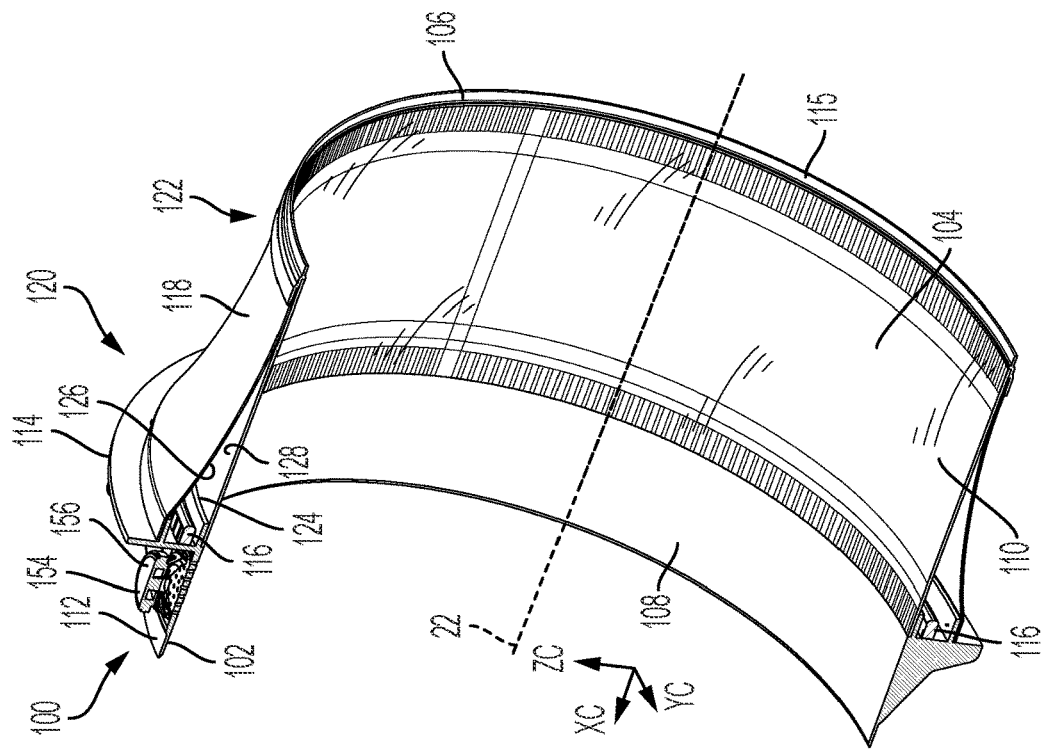
FIGS. 5 and 6 are perspective and cross-sectional views, respectively, of a further alternate embodiment of a lighting arrangement for illuminating the tunnel.
Figure 5:
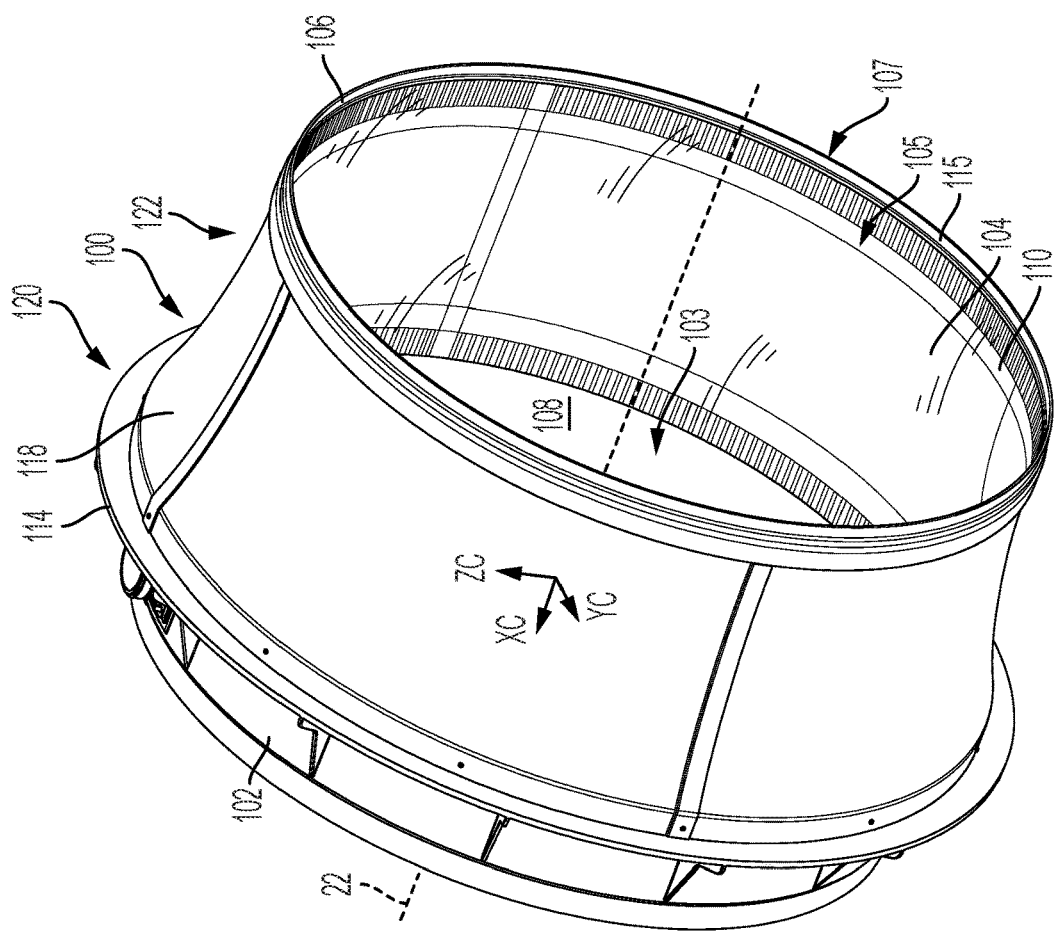

FIGS. 5 and 6 are perspective and cross-sectional views, respectively, of a further alternate embodiment of a lighting arrangement 100 for illuminating the tunnel 32 (FIG. 2A). The lighting arrangement 100 includes annular bezel 102, light transmitting 104 and mounting trim 106 sections having first 103, second 105 and third 107 apertures that define first 108, second 110 and third 115 inner surfaces, respectively. Inner surface 108 of the bezel section 102, inner surface 110 of the light transmitting section 104 and inner surface 115 of the mounting trim section 106 are substantially aligned with the inner surface 50 of the tunnel wall 46 (see FIG. 2A). The longitudinal axis 22 extends through the first 103, second 105 and third 107 central apertures. The light transmitting section 104 is located between the bezel 102 and mounting trim 106 sections and is sufficiently sized in the longitudinal direction to provide circumferential illumination of the tunnel 32 to help ease a patient's feeling of claustrophobia while in the tunnel 32.

An outer surface 112 of the bezel section 102 includes a circumferential upstanding flange portion 114 that includes at least one lighting device 116 (see also FIGS. 8 and 9). The lighting device 116 is arranged circumferentially on the flange portion 114 and extends toward the light transmitting section 104. In an aspect of the invention, the lighting device 116 may include at least one strip of LED lights that is mounted circumferentially around the bezel section 102. In addition, a protective barrier may be positioned between the LED lights to prevent light "hot spots" at an LED mounting location. In addition, the outer surface 112 may include a microphone 154 and speaker 156 to enable communication between a patient and an operator of the system.

The lighting arrangement 100 further includes a reflector section 118 having a first end 120 removably attached to the flange portion 114 and a second 122 end removably attached to the mounting trim section 106. In an aspect of the invention, a size of the reflector section 118 in the longitudinal direction substantially corresponds to the size of the transmitting section 104 in the longitudinal direction. Alternatively, the reflector section 118 and transmitting section 104 may differ in size relative to each other in the longitudinal direction. The reflection section 118 is radially outside the light transmitting section 104, relative to the longitudinal axis 22, to form a cavity 124. In an aspect of the invention, the reflector section 118 tapers toward the longitudinal axis 22 between the first 120 and second 122 ends to form a substantially tapered shape. The lighting device 116 is located in the cavity 124 between the reflector section 118 and the light transmitting section 104. Light emitted by the lighting device 116 is reflected by a reflector inner surface 126 toward an outer surface 128 of the light transmitting section 104. The light transmitting section 104 receives the light and transmits the light into the tunnel 32 to circumferentially illuminate the tunnel 32 in a longitudinal direction. Illumination of the tunnel 32 provides comfort to a patient located within the tunnel 32 and helps ease a feeling of claustrophobia while in the tunnel 32. In an aspect of the invention, the light transmitting section 104 is fabricated from a light diffusing material. For example, the light diffusing material may be fabricated from a light diffusing plastic or equivalent material that diffuses, scatters or filters the light emitted by the lighting device 116 such that the light fades as the light travels away from the lighting device 116 and the light transmitting section 104 glows. Alternatively, substantially uniform lighting may be achieved by varying the design of the reflector section 118 and the longitudinal length of the reflector section 118.

The invention may be used in conjunction with any medical imaging system 10 (FIG. 1) having a patient tunnel 32 for receiving a patient such as a magnetic resonance imaging (MRI) system, a positron emission tomography (PET) system, a single-photon emission computed tomography (SPECT) system, an X-ray computed tomography (CT) system. The invention may also be used in imaging systems having more than one type of imaging modality such as imaging systems wherein either a first imaging portion is a PET portion having a PET field of view and a second imaging portion is a CT portion having a CT field of view (PET/CT imaging system), the first imaging portion is a SPECT portion having a SPECT field of view and the second imaging portion is a CT portion having a CT field of view (SPECT/CT imaging system), the first imaging portion is a PET imaging portion having a PET field of view and the second imaging portion is an MR imaging portion having an MR field of view (PET/MRI imaging system) or the first imaging portion is an MR imaging portion having an MR field of view and the second imaging portion is a CT portion having a CT field of view.

Figure 7:
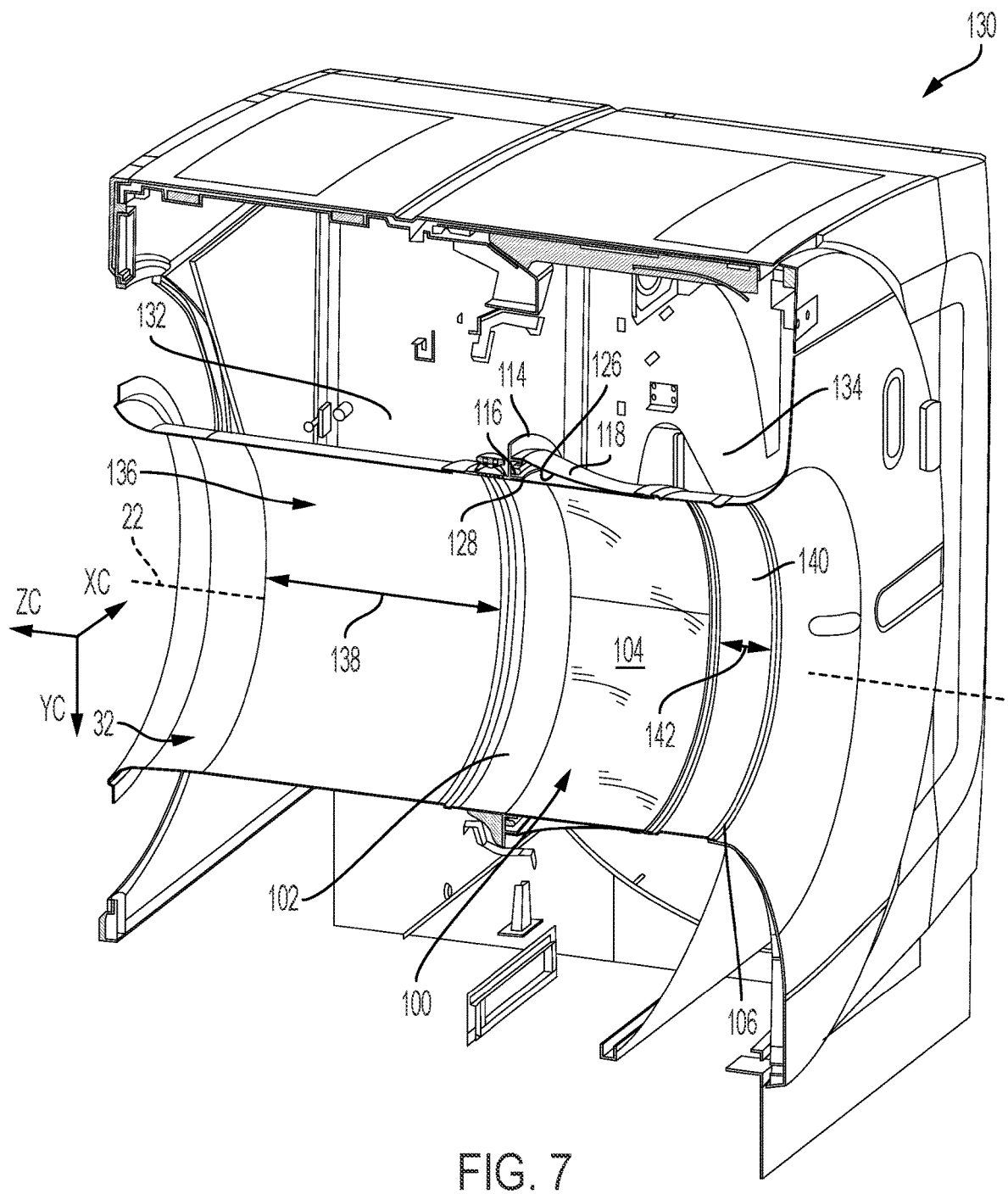
FIG. 7 is a partial cross-sectional view of a dual modality imaging system having first and second imaging portions.

FIG. 7 is a partial cross-sectional view of a dual modality imaging system 130 having a first imaging portion 132 that provides a first imaging modality and a second imaging portion 134 that provides a second imaging modality different from the first imaging modality. The first imaging portion 132 includes a first field of view 136 having a first width 138 and the second imaging portion 134 includes a second field of view 140 having a second width 142. In accordance with an aspect of the invention, the lighting arrangement 100 may be located between the first 136 and second 140 fields of view to limit artifacts and/or attenuation in the first 136 or second 140 fields of view. In an aspect of the invention, the lighting arrangement 100 is oriented such that that bezel section 102 is located adjacent to the first field of view 136 and the mounting trim section 106 is adjacent the second field of view 140. In this orientation, light emitted by the lighting device 116 is emitted toward the second imaging portion 134 and then reflected by the reflector inner surface 126 toward the outer surface 128 of the light transmitting section 104 as previously described in relation to FIG. 6. Alternatively, the lighting arrangement 100 may be oriented in an opposite direction such that the lighting device 116 emits light toward the first imaging portion 132. For example, the dual modality imaging system 130 may be a PET/CT imaging system that includes a PET imaging portion (first imaging portion 132) and a CT imaging portion (second imaging portion 134). The PET portion includes a PET field of view (first field of view 136) having a first width (first width 138) and the CT portion includes a CT field of view (second field of view 140) having a second width (second width 142). The lighting arrangement 100 is located between the PET and CT fields of view to limit artifacts and/or attenuation in the PET or CT fields of view.

FIG. 8 is a cross-sectional side view of the lighting arrangement. FIG. 9 is an enlarged view of balloon section 9 and depicts portions of the reflector section 118 and flange portion 114. The flange portion 114 includes a circumferential mounting member 144 that extends from the flange portion 114. The first end 120 of the reflector section 118 includes an attachment member 146 having an orientation that corresponds to the mounting member 144. The attachment member 146, and thus the reflector section 188, is removably attached to the mounting member 144 by a removable fastener 148 or other attachment device or attachment method. A first portion 152 of the reflector section 118 after the attachment member 146 tapers toward the longitudinal axis 22. FIG. 10 is an enlarged view of balloon section 10. The mounting trim section 106 includes a circumferential channel 150 that receives the second end 122 of the reflector section 118 to removably attach the reflector section 118 when the attachment member 146 is removably attached to the mounting member 144 of the flange portion 114.

The lighting arrangement 100 facilitates an infield upgrade of an operational imaging system by enabling the addition of at least one lighting device, such as an LED strip, to the imaging system 130 rather than replacing substantial portions of the tunnel 32 of the imaging system 130 to add lighting. This enables an operator to purchase an imaging system 130 with the option of adding lighting to the tunnel 32 at a future time in a cost-effective way. Further, the reflector section 118 is removably attached so that the lighting device 116 may be added or replaced in the field to further reduce costs.

In another aspect of the invention, a lighting device 116, such as LEDs, may be circumferentially located at first and second ends of the tunnel 32 such that they emit light toward each other. In still another aspect of the invention, a lighting device 116 may be circumferentially positioned relative to an outer diameter of a tunnel section fabricated from light diffusing plastic. The lighting device 116 may be positioned approximately 3-4 inches from the light diffusing plastic to reduce LED hot spots. Alternatively, a matrix of LED lights may be circumferentially positioned around the outer diameter of the tunnel section.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A lighting arrangement for a medical imaging system having a cylindrical wall that forms a tunnel that receives a patient to be scanned wherein the medical imaging system includes first and second imaging portions having first and second fields of view, respectively, comprising:
    a light transmitting section aligned on a longitudinal axis of the imaging system wherein the light transmitting section forms a part of the tunnel;
    a reflector section that is radially outside the light transmitting section;
    at least one lighting device located between the reflector section and light transmitting section wherein the lighting device emits light that is reflected by the reflector section onto the light transmitting section and wherein the light is then transmitted through the light transmitting section and into the tunnel to circumferentially illuminate the tunnel.

2. The lighting arrangement according to claim 1, wherein the light transmitting section is located between the first and second fields of view.

3. The lighting arrangement according to claim 1, wherein the reflector section is tapered.

4. The lighting arrangement according to claim 1, wherein the lighting device includes at least one strip of LED lights.

5. The lighting arrangement according to claim 1, wherein illumination of the tunnel by the lighting device ameliorates a patient's feeling of claustrophobia while in the tunnel.

6. The lighting arrangement according to claim 1, wherein the light transmitting section is fabricated from a light diffusing material.

7. The lighting arrangement according to claim 1, wherein the reflector section is removably attached to the lighting arrangement.

8. The lighting arrangement according to claim 1, wherein either the first imaging portion is a PET portion having a PET field of view and the second imaging portion is a CT portion having a CT field of view, the first imaging portion is a SPECT portion having a SPECT field of view and the second imaging portion is a CT portion having a CT field of view, the first imaging portion is an MR imaging portion having an MR field of view and the second imaging portion is a PET portion having a PET field of view or the first imaging portion is an MR portion having an MR field of view and the second imaging portion is a CT portion having a CT field of view.

9. A lighting arrangement for a medical imaging system having a cylindrical wall that forms a tunnel that receives a patient to be scanned wherein the medical imaging system includes first and second imaging portions having first and second fields of view, respectively, comprising:
   an annular light transmitting section located adjacent a bezel section, wherein the light transmitting and bezel sections are aligned on a longitudinal axis of the imaging system and form a part of the tunnel and wherein the bezel section includes a flange element;
   a reflector section that is radially outside the light transmitting section to form a cavity; and
   at least one lighting device arranged on the flange element and located between the reflector section and light transmitting section wherein the lighting device emits light into the cavity that is reflected by the reflector section onto the light transmitting section and wherein the light is then transmitted through the light transmitting section and into the tunnel to circumferentially illuminate the tunnel.

10. The lighting arrangement according to claim 9, wherein the light transmitting section is located between the first and second fields of view.

11. The lighting arrangement according to claim 9, wherein the reflector section is tapered.

12. The lighting arrangement according to claim 9, wherein the lighting device includes at least one strip of LED lights.

13. The lighting arrangement according to claim 9, wherein illumination of the tunnel by the lighting device ameliorates a patient's feeling of claustrophobia while in the tunnel.

14. The lighting arrangement according to claim 9, wherein the light transmitting section is fabricated from a light diffusing material.

15. The lighting arrangement according to claim 9, wherein the reflector section is removably attached to the lighting arrangement.

16. A method of illuminating a tunnel of a medical imaging system having a cylindrical wall that forms a tunnel that receives a patient to be scanned wherein the medical imaging system includes first and second imaging portions having first and second fields of view, respectively, comprising:
   providing a light transmitting section aligned on a longitudinal axis of the imaging system wherein the light transmitting section forms a part of the tunnel;
   providing a reflector section that is radially outside the light transmitting section; and
   providing light that is reflected by the reflector section onto the light transmitting section wherein the light is then transmitted through the light transmitting section and into the tunnel to circumferentially illuminate the tunnel.

17. The method according to claim 16, wherein the light transmitting section is located between the first and second fields of view.

18. The method according to claim 16, wherein the reflector section is tapered.

19. The method according to claim 16, wherein the light is provided by a lighting device that includes at least one strip of LED lights.

20. The method according to claim 16, wherein illumination of the tunnel ameliorates a patient's feeling of claustrophobia while in the tunnel.

21. The method according to claim 16, wherein the light transmitting section is fabricated from a light diffusing material.

22. The method according to claim 16, wherein the reflector section is removably attached to the light transmitting section.

* * * * *